(12) United States Patent
Bierman

(10) Patent No.: US 10,792,470 B2
(45) Date of Patent: Oct. 6, 2020

(54) FLEXIBLE MEDICAL ARTICLE AND METHOD OF MAKING THE SAME

(71) Applicant: Smiths Medical ASD, Inc., Plymouth, MN (US)

(72) Inventor: Steven F. Bierman, Del Mar, CA (US)

(73) Assignee: Smiths Medical ASD, Inc., Plymouth, MN (US)

(*) Notice: Subject to any disclaimer, the term of this patent is extended or adjusted under 35 U.S.C. 154(b) by 306 days.

(21) Appl. No.: 15/985,451

(22) Filed: May 21, 2018

(65) Prior Publication Data

US 2018/0264235 A1 Sep. 20, 2018

Related U.S. Application Data

(62) Division of application No. 14/385,135, filed as application No. PCT/US2013/031040 on Mar. 13, 2013, now Pat. No. 9,981,113.

(Continued)

(51) Int. Cl.
*A61M 25/06* (2006.01)
*B29C 48/09* (2019.01)
(Continued)

(52) U.S. Cl.
CPC .... *A61M 25/0606* (2013.01); *A61M 25/0009* (2013.01); *A61M 25/0043* (2013.01);
(Continued)

(58) Field of Classification Search
CPC .............. B29C 48/92; B29C 2071/022; B29C 2791/002; B29C 48/0011; B29C 48/0022;
(Continued)

(56) References Cited

U.S. PATENT DOCUMENTS 4,155,889 A 5/1979 Fagerburg et al.
4,963,306 A 10/1990 Weldon
(Continued)

FOREIGN PATENT DOCUMENTS

EP 0927559 7/1999
EP 1344549 9/2003
(Continued)

OTHER PUBLICATIONS

U.S. Appl. No. 16/191,122, filed Nov. 14, 2018, Bierman et al.
(Continued)

*Primary Examiner* — Jason E Flick
(74) *Attorney, Agent, or Firm* — Benesch, Friedlander, Coplan & Aronoff LLP

(57) ABSTRACT

A method of making a flexible medical article or tube, for example, a sheath for a vascular access device, is provided. The method can include extruding a polymer, for example, a polycarbonate-urethane copolymer, to form a tube and annealing the extruded polymer. The method can further include cutting the extruded tube to a desired length before or after annealing, flaring one end of the annealed tube and over-molding the flared portion onto a hub, and forming the other end of the tube into a tip. A sheath formed by such a method is also provided.

23 Claims, 6 Drawing Sheets

Related U.S. Application Data

(60) Provisional application No. 61/610,885, filed on Mar. 14, 2012.

(51) Int. Cl.

| | | |
|---|---|---|
| *B29C 48/10* | (2019.01) | |
| *B29C 48/00* | (2019.01) | |
| *B29C 48/91* | (2019.01) | |
| *A61M 25/00* | (2006.01) | |
| *B29C 48/13* | (2019.01) | |
| *B29C 48/88* | (2019.01) | |
| *B29C 71/02* | (2006.01) | |
| *B29C 48/92* | (2019.01) | |
| *B29K 69/00* | (2006.01) | |
| *A61M 29/00* | (2006.01) | |
| *B29C 48/11* | (2019.01) | |
| *B29C 57/02* | (2006.01) | |
| *B29D 23/00* | (2006.01) | |
| *B29K 75/00* | (2006.01) | |
| *B29L 23/00* | (2006.01) | |
| *B29L 23/20* | (2006.01) | |
| *B29L 31/00* | (2006.01) | |

(52) U.S. Cl.
CPC ...... *B29C 48/0011* (2019.02); *B29C 48/0022* (2019.02); *B29C 48/022* (2019.02); *B29C 48/09* (2019.02); *B29C 48/10* (2019.02); *B29C 48/13* (2019.02); *B29C 48/88* (2019.02); *B29C 48/91* (2019.02); *B29C 48/9105* (2019.02); *B29C 71/02* (2013.01); *A61M 25/001* (2013.01); *A61M 29/00* (2013.01); *A61M 2025/0059* (2013.01); *A61M 2025/0064* (2013.01); *B29C 48/11* (2019.02); *B29C 48/913* (2019.02); *B29C 48/92* (2019.02); *B29C 57/02* (2013.01); *B29C 2071/022* (2013.01); *B29C 2791/002* (2013.01); *B29D 23/001* (2013.01); *B29K 2069/00* (2013.01); *B29K 2075/00* (2013.01); *B29L 2023/00* (2013.01); *B29L 2023/007* (2013.01); *B29L 2023/20* (2013.01); *B29L 2031/7542* (2013.01)

(58) Field of Classification Search
CPC ....... B29C 48/022; B29C 48/09; B29C 48/10; B29C 48/11; B29C 48/91; B29C 48/9105; B29C 48/913; B29C 57/02; B29C 71/02; B29C 48/13; B29C 48/88; A61M 2025/0059; A61M 2025/0064; A61M 25/0009; A61M 25/001; A61M 25/0043; A61M 25/0606; A61M 29/00; B29D 23/001; B29K 2069/00; B29K 2075/00; B29L 2023/00; B29L 2023/007; B29L 2023/20; B29L 2031/7542
See application file for complete search history.

(56) References Cited

U.S. PATENT DOCUMENTS

| | | | |
|---|---|---|---|
| 5,133,336 A | 7/1992 | Savitt et al. | |
| 5,199,417 A | 4/1993 | Muller et al. | |
| 5,229,431 A | 7/1993 | Pinchuk | |
| 5,254,662 A | 10/1993 | Szycher et al. | |
| 5,316,706 A | 5/1994 | Muni et al. | |
| 5,348,538 A | 9/1994 | Wang et al. | |
| 5,735,793 A | 4/1998 | Takahashi et al. | |
| 5,741,452 A | 4/1998 | Ryan et al. | |
| 5,782,811 A | 7/1998 | Samson et al. | |
| 5,895,378 A | 4/1999 | Berenstein et al. | |
| 5,938,653 A | 8/1999 | Pepin | |
| 5,948,345 A | 9/1999 | Patel et al. | |
| 5,951,494 A | 9/1999 | Wang et al. | |
| 5,971,975 A | 10/1999 | Mills et al. | |
| 6,129,876 A | 10/2000 | Qin et al. | |
| 6,197,014 B1 | 3/2001 | Samson et al. | |
| 6,221,097 B1 | 4/2001 | Wang et al. | |
| 6,524,299 B1 | 2/2003 | Tran et al. | |
| 6,726,659 B1 | 4/2004 | Stocking et al. | |
| 7,011,872 B2 | 3/2006 | Ding et al. | |
| 7,025,746 B2 | 4/2006 | Tal | |
| 7,182,755 B2 | 2/2007 | Tal | |
| D594,981 S | 6/2009 | Bierman et al. | |
| D600,793 S | 9/2009 | Bierman et al. | |
| D601,242 S | 9/2009 | Bierman et al. | |
| D601,243 S | 9/2009 | Bierman et al. | |
| D615,201 S | 5/2010 | Bierman et al. | |
| 7,722,567 B2 | 5/2010 | Tal | |
| D617,893 S | 6/2010 | Bierman et al. | |
| D624,643 S | 9/2010 | Bierman et al. | |
| D630,729 S | 1/2011 | Bierman et al. | |
| 7,922,696 B2 | 4/2011 | Tal et al. | |
| 7,931,619 B2 | 4/2011 | Diamond et al. | |
| 8,105,286 B2 | 1/2012 | Anderson et al. | |
| 8,192,402 B2 | 6/2012 | Anderson et al. | |
| 8,202,251 B2 | 6/2012 | Bierman et al. | |
| 8,377,006 B2 | 2/2013 | Tal et al. | |
| 8,657,790 B2 | 2/2014 | Tal et al. | |
| 8,672,888 B2 | 3/2014 | Tal | |
| 8,747,878 B2 | 6/2014 | Huang et al. | |
| 8,827,958 B2 | 9/2014 | Bierman et al. | |
| 8,900,192 B2 | 12/2014 | Anderson et al. | |
| 8,915,884 B2 | 12/2014 | Tal et al. | |
| 8,956,327 B2 | 2/2015 | Bierman et al. | |
| 8,974,426 B2 * | 3/2015 | Corcoran ......... | A61M 25/0009 604/264 |
| 9,138,252 B2 | 9/2015 | Bierman et al. | |
| 9,566,087 B2 | 2/2017 | Bierman et al. | |
| 9,764,117 B2 | 9/2017 | Bierman et al. | |
| 9,884,169 B2 | 2/2018 | Bierman et al. | |
| 9,981,113 B2 | 5/2018 | Bierman | |
| 10,010,343 B2 | 7/2018 | Bierman et al. | |
| 10,136,916 B2 | 11/2018 | Bierman et al. | |
| 10,441,752 B2 | 10/2019 | Bierman et al. | |
| 2001/0001113 A1* | 5/2001 | Lim ..................... | B29C 48/21 604/96.01 |
| 2002/0002363 A1 | 1/2002 | Urakawa et al. | |
| 2002/0072712 A1 | 6/2002 | Nool et al. | |
| 2003/0006610 A1 | 1/2003 | Werth | |
| 2003/0055402 A1 | 3/2003 | Zhou | |
| 2004/0159968 A1 | 8/2004 | Lee et al. | |
| 2005/0033237 A1 | 2/2005 | Fentress et al. | |
| 2006/0096597 A1 | 5/2006 | Amann | |
| 2006/0264904 A1 | 11/2006 | Kerby et al. | |
| 2007/0197855 A1 | 8/2007 | Richardson et al. | |
| 2008/0051759 A1 | 2/2008 | Murphy et al. | |
| 2008/0255417 A1 | 10/2008 | Bob | |
| 2008/0262431 A1 | 10/2008 | Anderson et al. | |
| 2009/0179422 A1 | 7/2009 | Werth | |
| 2009/0221961 A1 | 9/2009 | Tal et al. | |
| 2009/0306327 A1 | 12/2009 | Stewart et al. | |
| 2010/0224276 A1* | 9/2010 | Forrester ......... | A61M 16/0875 138/122 |
| 2010/0252965 A1 | 10/2010 | Wang et al. | |
| 2011/0021994 A1 | 1/2011 | Anderson et al. | |
| 2011/0124772 A1* | 5/2011 | Wang .................... | A01N 33/12 523/177 |
| 2011/0202006 A1 | 8/2011 | Bierman et al. | |
| 2011/0215505 A1 | 9/2011 | Kleiner et al. | |
| 2011/0218496 A1 | 9/2011 | Bierman | |
| 2011/0220270 A1 | 9/2011 | Koori | |
| 2011/0276002 A1 | 11/2011 | Bierman | |
| 2012/0041419 A1 | 2/2012 | Blanchard et al. | |
| 2012/0283640 A1 | 11/2012 | Bierman et al. | |
| 2013/0092277 A1 | 4/2013 | Garrett et al. | |
| 2014/0025036 A1 | 1/2014 | Bierman et al. | |
| 2014/0081210 A1 | 3/2014 | Bierman et al. | |
| 2014/0207069 A1 | 7/2014 | Bierman et al. | |
| 2015/0126930 A1 | 5/2015 | Bierman et al. | |
| 2015/0190168 A1 | 7/2015 | Bierman et al. | |

(56) References Cited

U.S. PATENT DOCUMENTS

| | | |
|---|---|---|
| 2015/0297868 A1 | 10/2015 | Tal et al. |
| 2015/0351793 A1 | 12/2015 | Bierman et al. |
| 2017/0035459 A1 | 2/2017 | Bierman et al. |
| 2017/0043100 A1 | 2/2017 | Nguyen et al. |
| 2018/0001060 A1 | 1/2018 | Bierman et al. |
| 2018/0221628 A1 | 8/2018 | Bierman |
| 2018/0264234 A1 | 9/2018 | Bierman |
| 2018/0271558 A1 | 9/2018 | Bierman |
| 2018/0296804 A1 | 10/2018 | Bierman |
| 2019/0076166 A1 | 3/2019 | Bierman |
| 2019/0269890 A1 | 9/2019 | Bierman |

FOREIGN PATENT DOCUMENTS

| | | |
|---|---|---|
| JP | 03-73167 | 3/1991 |
| WO | WO 1998/44979 | 10/1998 |
| WO | WO 99/24084 | 5/1999 |
| WO | WO 04/028611 | 4/2004 |
| WO | WO 06/122155 | 11/2006 |
| WO | WO 07/095040 | 8/2007 |
| WO | WO 08/024514 | 2/2008 |
| WO | WO 08/131289 | 10/2008 |
| WO | WO 13/138519 | 9/2013 |

OTHER PUBLICATIONS

U.S. Appl. No. 15/942,217, filed Mar. 30, 2018, Bierman.
U.S. Appl. No. 15/985,405, filed May 21, 2018, Bierman.
U.S. Appl. No. 15/995,512, filed Jun. 1, 2018, Bierman et al.
Examination Report received in Application No. EP 13760352.8 dated May 11, 2018.
U.S. Appl. No. 29/375,448, filed Sep. 22, 2010, Bierman et al.
U.S. Appl. No. 14/831,704, filed Aug. 20, 2015, Bierman et al.
U.S. Appl. No. 15/703,026, filed Sep. 13, 2017, Bierman et al.
U.S. Appl. No. 15/887,170, filed Feb. 2, 2018, Bierman et al.
Christenson, E.M., et al., Biodegradation Mechanisms of Polyurethane Elastomers, Corrosion Engineering, Science and Technology, vol. 42, No. 4, Dec. 1, 2007, pp. 312-323.
Cipriani, E., et al., Thermoplastic Polyurethanes with Polycarbonate Soft Phase: Effect of Thermal Treatment on Phase Morphology, Polymer Degradation and Stability, Sep. 1, 2012, pp. 1794-1800.
Examination Report received in Application No. EP 13760352.8 dated Dec. 1, 2016.
Examination Report received in Application No. EP 13760352.8 dated Sep. 29, 2017.
International Preliminary Report on Patentability received in Application No. PCT/US2013/031040 dated Sep. 16, 2014.
International Search Report and Written Opinion received in Application No. PCT/US2013/031040 dated May 31, 2013.
Koenen, J., Orthopedic Implant Materials of DSM Biomedical BV, European Medical Polymers Conference, Sep. 9, 2010, pp. 1-26.
Malinin, et al.: "Design of Medical Devices That Meet Contradictory Requirements," The Open Medical Devices Journal, 2011, 3, 9-18.
Processing Guidelines ISOPLAST Engineering TPU Resins, Nov. 14, 2009, pp. 1-12.
Supplementary European Search Report received in Application No. EP 13760352.8 dated Sep. 15, 2015.

* cited by examiner

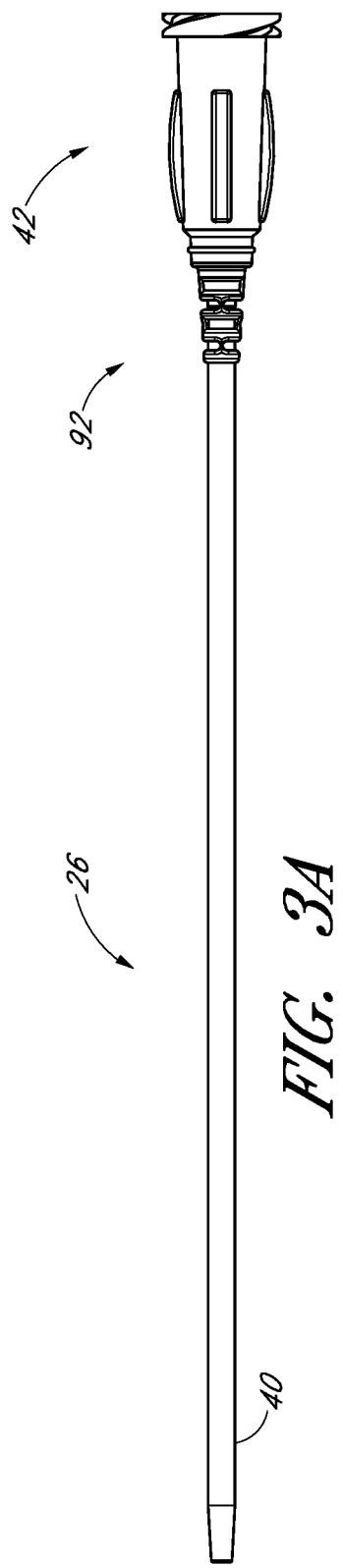

FLEXIBLE MEDICAL ARTICLE AND METHOD OF MAKING THE SAME

CROSS-REFERENCE TO RELATED APPLICATIONS

Any and all applications for which a foreign or domestic priority claim is identified in the Application Data Sheet as filed with the present application are hereby incorporated by reference under 37 CFR 1.57. This application is a Divisional application of U.S. application Ser. No. 14/385,135, filed Sep. 12, 2014, which is a National Phase Application of PCT International Application Number PCT/US2013/031040, filed Mar. 13, 2013, which claims the benefit of priority under 35 U.S.C. § 119(e) of U.S. Provisional Application No. 61/610,885 filed on Mar. 14, 2012, the entirety of each of which is incorporated herein by reference.

BACKGROUND OF THE INVENTION

Field of the Invention

The present disclosure is generally directed to methods for making a medical article (for example, catheters, cannulas, and sheaths) for the introduction and/or delivery into a body space, such as, for example, an artery, vein, vessel, body cavity, or drainage site. The disclosure is also directed to such medical articles and to access devices that place such medical articles into an artery, vein, vessel, body cavity, or drainage site.

Description of the Related Art

Various medical articles, for example, catheters, cannulas, sheaths, etc., are often introduced into a patient, for example, in an artery, vein, body cavity, or drainage site, to deliver fluids to, or withdraw fluids from, the patient. For example, a catheter or vascular sheath can be introduced into a patient's blood vessel using the Seldinger or a modified Seldinger technique. These techniques involve inserting an access needle into the patient's blood vessel and then inserting a guidewire through the needle and into the vessel. The needle is removed, and a dilator and sheath, either separately, or in combination, are inserted over the guidewire, through tissue, and into the vessel. The dilator and guidewire are then removed and discarded. The sheath can be left in the vessel, for example, to deliver medical fluids to the patient, or a catheter or other medical article can be inserted through the sheath into the vessel to a desired location.

A medical provider may need to bend and manipulate the sheath and/or catheter during insertion and/or after insertion during use. Although some existing sheaths and catheters have some flexibility to allow for such manipulation, existing devices may kink when bent to a certain radius of curvature, for example, a 90 degree bend. When medical articles kink, they can disrupt the flow of fluids within the device and hinder performance of the device. Additionally, some sheaths and catheters are more prone to re-kink or re-crease after initially kinking and may subsequently kink at an earlier point, for example, at a smaller angle of bending.

SUMMARY

In view of the foregoing, there is a need for an improved medical article and method of making such a medical article with improved flexibility, memory, kink-resistance, and/or resilience.

In some embodiments, a method for forming a flexible medical article includes extruding a polymer, for example, a polycarbonate-urethane copolymer or another form of urethane. The method can further include heat treating the flexible medical article by annealing under conditions of, for example, 248° F. for one hour. In some embodiments, the polymer is selected have the property of reduced rigidity (i.e., increased flexibility) when exposed to heat. The method can further include cutting the medical article into desired lengths before and/or after annealing. Optionally, the method can also include flaring one end of the medical article to be coupled to a hub and over-molding the flared end onto the hub and/or forming one end of the medical article into a tip.

In some embodiments, a method for forming a flexible medical article includes extruding a polymer, for example, a polycarbonate-urethane copolymer or another form of urethane, to form a tubular shaft with at least one lumen. The method can further include heat treating the tubular shaft by annealing under conditions of, for example, 248° F. for one hour. In some embodiments, the polymer is selected have the property of reduced rigidity (i.e., increased flexibility) when exposed to heat. The method can further include cutting the tubular shaft into desired lengths before and/or after annealing. The method can also include flaring one end of the tubular shaft to be coupled to a hub and over-molding the flared end onto the hub and/or forming one end of the tube into a tip. In one embodiment, the tubular shaft is annealed sufficiently so as to be capable of bending up to about 120° without kinking. In another embodiment, the polymer is capable of withstanding pressures up to 300 psi and flow rates of up to 130 ml/min.

In some embodiments, a flexible medical article or tube which can be used as, for example, a sheath or catheter to be introduced into a body lumen of a patient is formed by extruding a polymer to form a tube and annealing the tube.

In one embodiment, the flexible medical article additionally comprises a needle having a needle shaft and a needle hub, a dilator having a dilator shaft and a dilator hub, and a guidewire, wherein the dilator shaft is coaxially disposed on the needle shaft with the needle hub and dilator hub juxtaposed, the guidewire is at least partially disposed in the needle, and the shaft is coaxially disposed on the dilator shaft with the hub juxtaposed the dilator hub.

In one embodiment, a method of using a medical article having a flexible shaft comprising annealed urethane polycarbonate comprises inserting the shaft into a vessel over a guidewire, withdrawing the guidewire, and bending the shaft to lie substantially parallel to the skin, and retaining the shaft in the bent position without kinking the shaft.

BRIEF DESCRIPTION OF THE DRAWINGS

The foregoing and other features, aspects, and advantages of the method of making a medical article and corresponding medical article are described in detail below with reference to the drawings of various embodiments, which are intended to illustrate and not to limit the embodiments of the invention. The drawings comprise the following figures of one embodiment, in which:

FIG. 3A is a plan view of a sheath from FIG. 1A and shows a sheath hub connected to a proximal end of a sheath.

DETAILED DESCRIPTION

Embodiments of the invention will now be described with reference to the accompanying figures, wherein like numerals refer to like elements throughout the following description and drawings. Although several embodiments, examples and illustrations are disclosed below, it will be understood by those of ordinary skill in the art that the invention described herein extends beyond the specifically disclosed embodiments, examples and illustrations and can include other uses of the invention and obvious modifications and equivalents thereof. The terminology used in the description presented herein is not intended to be interpreted in any limited or restrictive manner simply because it is being used in conjunction with a detailed description of certain specific embodiments of the invention. In addition, embodiments of the invention can comprise several novel features and no single feature is solely responsible for its desirable attributes or is essential to practicing the inventions herein described.

Figure 1A:
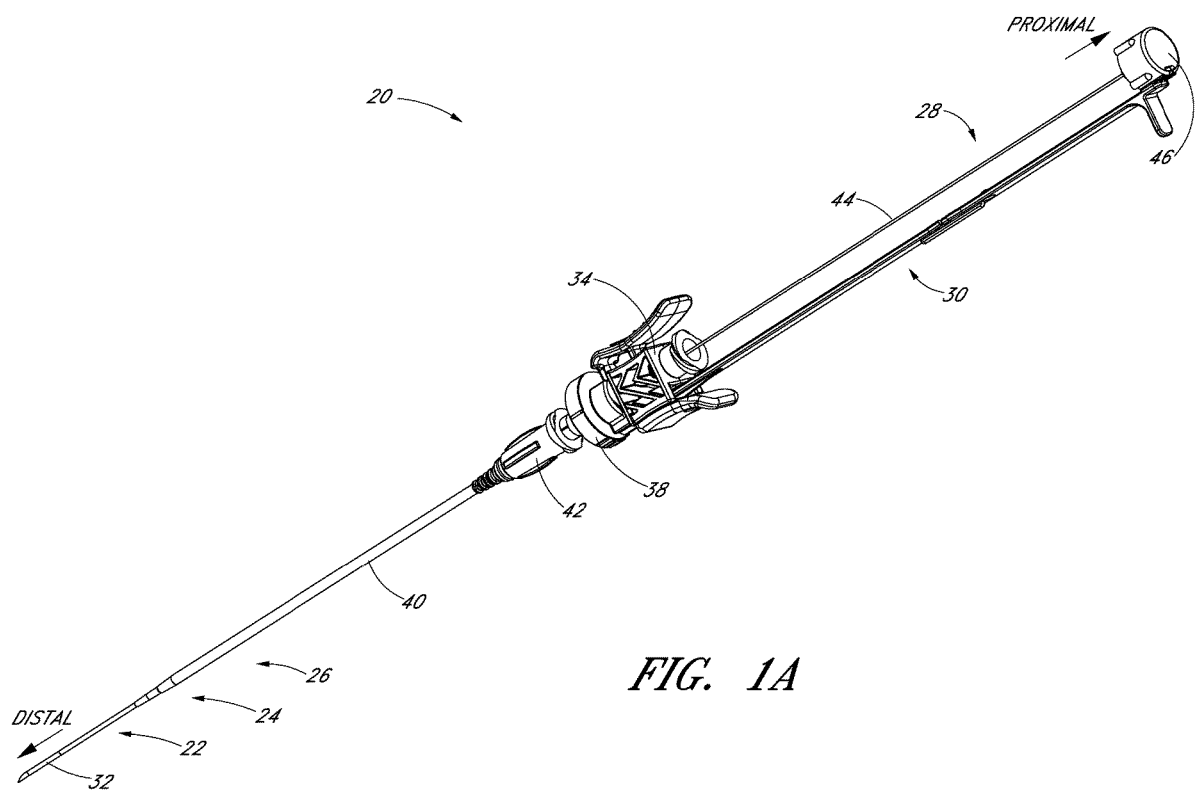
FIG. 1A is a perspective view of an embodiment of an access device.

The present disclosure provides a medical article (e.g., a catheter, cannula, or sheath) that can be delivered into a space, such as a blood vessel or drainage site, by an access device. FIG. 1A illustrates an access device 20 that is configured to be inserted into a blood vessel (e.g., a vein or an artery) in accordance with a preferred embodiment of the access device 20. While the access device 20 is described below in this context (i.e., for vascular access), the access device 20 also can be used to access and place the medical article into other locations within a patient's body (e.g., a drainage site) and for other purposes (e.g., for draining an abscess).

In various circumstances a medical provider may wish to introduce a catheter and/or sheath into a space within a patient's body, for example, a blood vessel or drainage site, to introduce fluids to the space or remove fluids from the space. Various access devices are known in the art. Examples of an improved access device are described in PCT Application No. PCT/US2012/039740, entitled "ACCESS DEVICE," filed May 25, 2012, which is incorporated by reference in its entirety herein.

The present embodiment of the access device is disclosed in the context of placing an exemplary single-piece, medical article into a body space within a patient. Once placed, the medical article can then be used to receive other medical articles (e.g., guidewires) to provide access into the body space and/or be used to provide a passage way for introducing fluids into the body space or removing (e.g., draining) fluids from the body space. In the illustrated embodiment in FIG. 1A, the medical article is a sheath 26 or catheter that is configured primarily to provide a fluid passage into a vein. The principles of the present invention, however, are not limited to the placement of single piece sheaths or catheters, or to the subsequent insertion of a medical article via the sheath or catheter. Instead, it will be understood in light of the present disclosure that the access device disclosed herein also can be successfully utilized in connection with placing one or more other types of medical articles, including other types of sheaths, fluid drainage and delivery tubes, and single or multi-lumen catheters directly in the patient or indirectly via another medical article.

For example, but without limitation, the access device disclosed herein can also be configured to directly or indirectly place central venous catheters, peripherally inserted central catheters, hemodialysis catheters, surgical drainage tubes, tear-away sheaths, multi-piece sheaths, PICC lines, IV lines, scopes, as well as electrical conduit for wires or cables connected to external or implanted electronic devices or sensors. As explained above, the medical articles listed above may be directly placed in the patient via the dilator, needle, and guidewire of the access device or subsequently placed within the patient via a medical article that was placed within the patient via the dilator, needle, and guidewire of the access device.

Further, the embodiments disclosed herein are not limited to co-axial insertion of a single medical article. For example, two catheters may be inserted in the patient via an inserted sheath or a second catheter may be inserted in the patient via an inserted first catheter. Further, in addition to providing a conduit into the vessel or other body space, the medical article inserted via the dilator, needle, and guidewire can form a lumen that is in addition to the lumen(s) of the subsequently inserted medical article. One skilled in the art can also find additional applications for the devices and systems disclosed herein. Thus, the illustration and description of the access device in connection with a sheath (e.g., for micro puncture applications) is merely exemplary of one possible application of the access device.

Figure 1B:
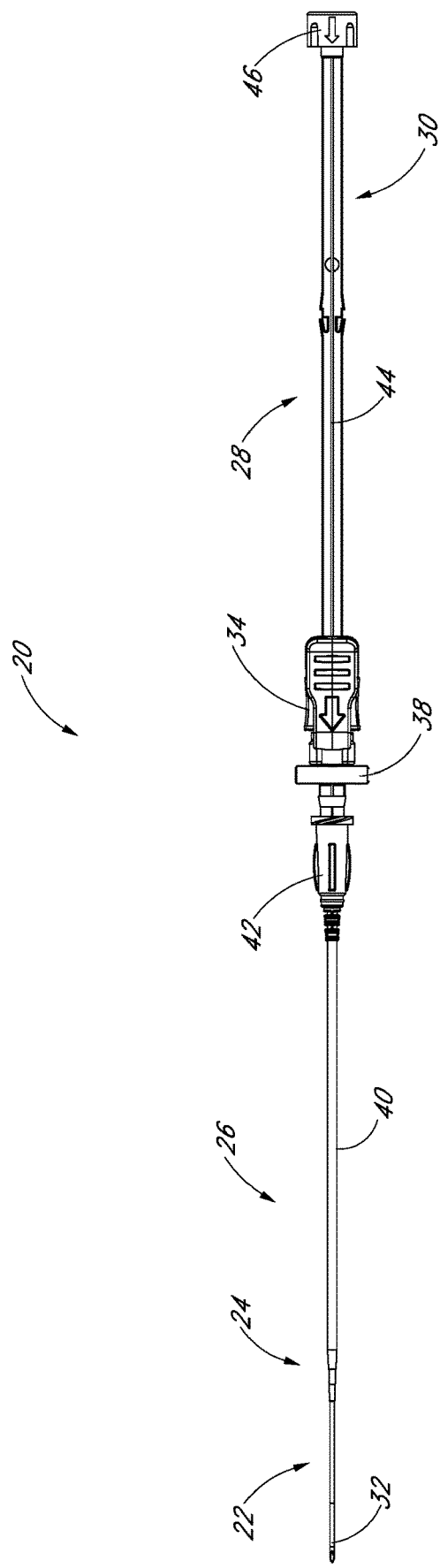
FIG. 1B is a plan view of the embodiment depicted in FIG. 1A.

FIGS. 1A and 1B illustrate a preferred embodiment of an access device 20. The access device 20 includes a needle 22, a dilator 24, and a sheath 26. In the illustrated embodiment, the access device also includes a guidewire section 28 and a track 30. As best seen in FIG. 1B, the dilator 24 can be coaxially mounted on the needle 22, and the sheath 26 can be coaxially mounted on the dilator 24. The telescoping nature of the access device's components can also be accomplished by arranging the components with their axes arranged substantially parallel rather than coaxially (e.g., a monorail-type design). In use, the dilator 24 and/or sheath 26 can slide distally over the needle 32 for insertion into a cavity and the needle hub 34 can slide relatively along the track 30.

Each of these components can include a luminal fitting at a terminal end or transition (e.g., a hub) and elongated structure that extends from the fitting. Thus, in the illustrated embodiment, the needle 22 includes a needle body 32 that extends distally from the needle hub 34, the dilator 24 includes a dilator shaft 36 that extends distally from a dilator hub 38, and the sheath 26 includes a sheath body 40 that extends distally from a sheath hub 42. The guidewire section 28 can include a guidewire 44 and preferably a guidewire hub or cap 46. In the illustrated embodiment, the guidewire hub 46 is disposed on the proximal end of the guidewire 44; however, in other applications, the hub 46 can be disposed at a location between the ends of the guidewire 44.

The needle body 32 can have a sufficiently long length to access a targeted subcutaneous body space and can have a sufficient gauge size to withstand the insertion forces when accessing the body space without causing undue trauma. For many applications, the needle body can have a length between 3-20 cm, and more preferably between 3-10 cm. For example, to access a body space (e.g., a vessel) in the thorax of an adult human, the needle body 32 preferably has a length of 7 cm or greater, and more preferably has a length of 9 cm or greater, and most preferably has a length of 9 to 10 cm. The size of the needle preferably is 18 gauge or smaller, and more preferably between 18-28 gauge, and most preferably between 18-26 gauge for micro-puncture applications (e.g., peripheral IVs). For applications with a neonate, the length and gauge of the needle body 32 should be significantly shorter and smaller, for example preferably between 3-4 cm and between 26-28 gauge.

As explained below in greater detail, the guidewire 44 can be introduced through a hollow and preferably tapered portion of the needle hub 34, through the needle body 32, and into a punctured vessel. Advantageously, the tapered portion can guide the guidewire 44 toward the bore of the needle 22. Further, in some embodiments this tapered portion can provide a female luer connection. The guidewire 44 allows the healthcare provider to guide the dilator 24 and sheath 26 into the vessel.

Figure 2:
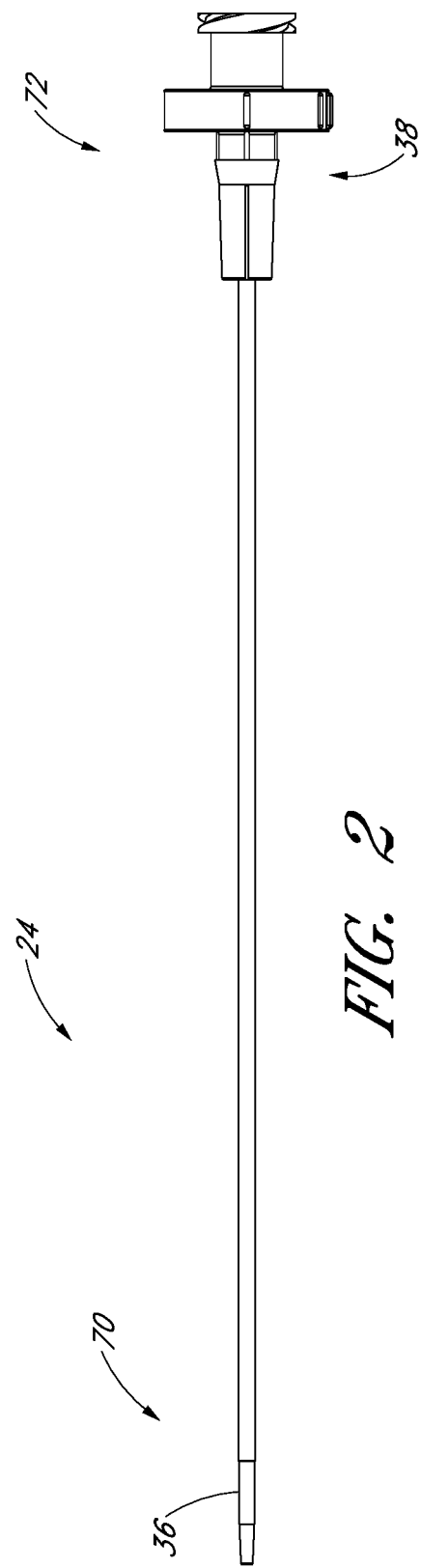
FIG. 2 is a plan view of a dilator from FIG. 1A.

FIG. 2 is a plan view of the dilator 24 of the embodiment depicted in FIG. 1A. As shown in FIG. 2, the illustrated dilator 24 can include a dilator shaft 36, a dilator hub 38, a distal region 70, and a proximal region 72. As described above, the dilator hub 38 can be a fitting at a terminal end supporting the dilator shaft 36.

Figure 3B:
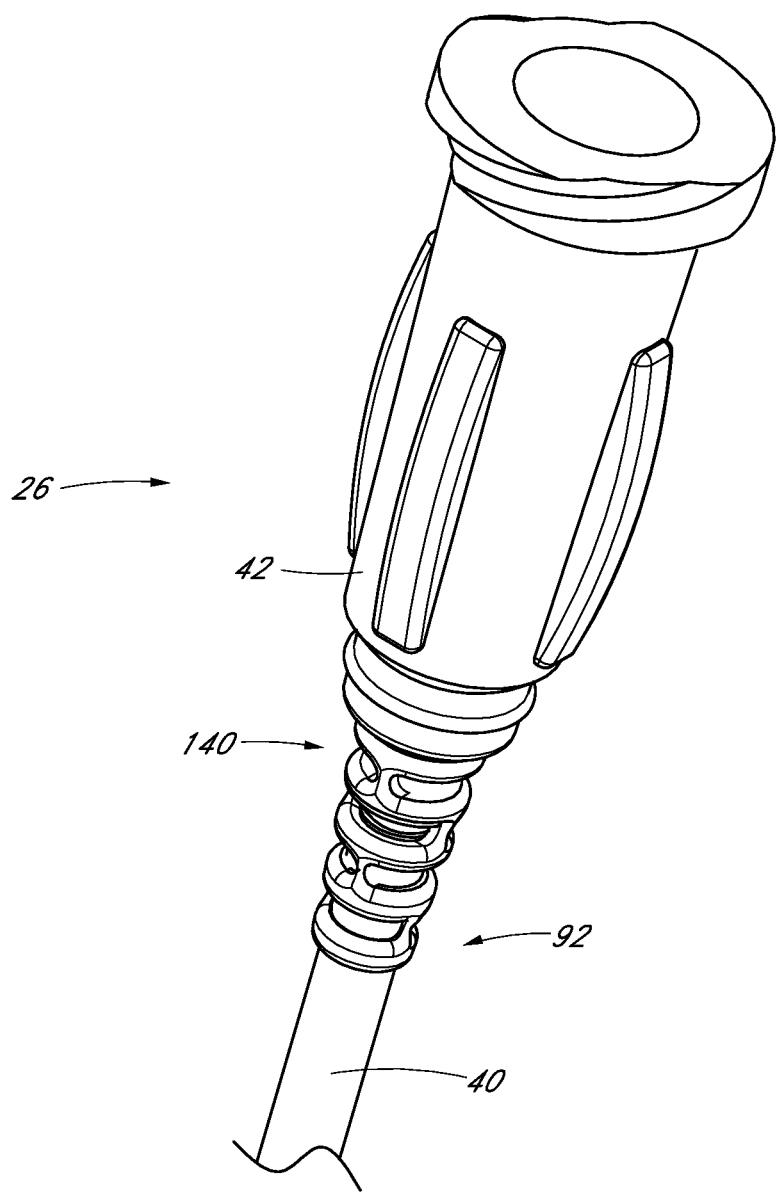
FIG. 3B is an enlarged perspective view of a proximal portion of the sheath from FIG. 3A.

FIG. 3A is a plan view of the sheath 26 of the embodiment depicted in FIG. 1A. FIG. 3B is an enlarged perspective view of the sheath hub 42 of the sheath 26 of FIG. 3A. As shown in FIGS. 3A and 3B, the sheath 26 can include a sheath body 40 and a sheath hub 42. The sheath body 40 may be made partially or completely from clear, translucent, transparent, or semi-opaque material. As described above, the sheath hub 42 can be a fitting at a terminal end supporting the sheath body 40.

In some embodiments, the sheath 26 can have relief elements 140, best illustrated in FIG. 3B, extending from the sheath hub 42 (e.g., a distal portion of the sheath hub 42). The relief elements 140 can be disposed about a proximal portion 92 of the sheath body 40, to provide support to the proximal portion 92 of the sheath body 40 when the proximal portion 92 flexes with respect to the sheath hub 42.

The relief element 140 can include a variety of shapes and structures to provide additional support to sheath body 40 while still providing some flexibility thereto. For example, the relief element 140 can include a substantially hollow elongated member, an approximately rectangular or cylindrical tubular shape, and can be configured with a wall thickness and material that provide some support and flexibility. The relief element 140 can be configured with a substantially continuous or unbroken surface, or can include gaps, apertures, recessions, or other structure extending partially or completely through its surface to provide additional flexibility against kinking. The relief element 140 can include various support structures such as circumferential or longitudinal (axial) ribs, struts, and the like.

In other embodiments, the relief element is absent. Improved patency of the bent medical article (e.g., the sheath) is obtained by the annealing process described below. In such embodiments, a short outer sleeve can extend from the sheath hub to the sheath shaft to form a relatively smooth transition region.

The sheath body 40 can be a single piece sheath through which fluid (e.g., an IV solution or imaging solution) is introduced into the vessel or withdrawn from the vessel. In one form, the sheath body 40 is an extended dwell (e.g., up to 29 days) peripheral catheter of 4 or 5 French having a single lumen with a length of about 80 mm. The sheath body 40 alternatively can be a single or multi-piece body through which other medical devices are introduced into the vessel. For example, a catheter or other medical article (e.g., a guidewire) can be inserted into the vessel through the sheath body. In such an embodiment, the sheath body 40 forms a conduit for insertion of the catheter or other medical article (e.g., a guidewire). In some embodiments, the sheath body 40 can be split along its length to ease removal of the sheath once the catheter or other medical article (e.g., PICC) has been placed in the patient. In some embodiment, the sheath or a portion of the sheath can, in addition to providing a conduit, form a lumen that is in addition to the lumen(s) of the catheter. For example, an equivalent to a triple lumen catheter can be formed by inserting a dual lumen catheter through the sheath body 40 with the sheath body 40 itself forming a third lumen.

During or after the insertion of sheath 26 into a patient, prior forms of the sheath body 40 could over-flex, kink, and/or permanently deform, which would reduce or inhibit its functionality. Prior sheath body 40 would thus be susceptible to such kinking or permanent deformation, for example, at the interface between sheath body 40 and the sheath hub 42, or at portions upstream or downstream of the interface between sheath body 40 and the sheath hub 42. A kink or permanent deformation would inhibit the flow of fluid, such as blood or medicine, through sheath body 40. Additionally, if access device 20 were used, for example, for IV lines, PICC lines, and other higher pressure applications, the proximal end of sheath body 40 could move erratically in a "whipping" motion as the pressurized fluid flows through sheath 26. To reduce the likelihood of such kinking or permanent deformation within sheath body 40, and/or to reduce the likelihood of such whipping during the deployment of access device 20, in some embodiments, sheath 26 can include various materials and an optional relief element 140, as described above, that can provide support to sheath 26.

In some embodiments, the sheath can be made of a material with sufficient flexibility to facilitate the insertion of the sheath into a patient and fluid transfers through the sheath. In some embodiments, the sheath can be made of a material that varies in flexibility depending on the environment to which it is exposed. For example, the sheath can be made of a material that varies in flexibility and/or rigidity based upon the temperature to which the sheath is exposed. In some embodiments, the sheath can be made of a material that has a reduced rigidity and/or increased flexibility upon exposure to heat, e.g., a temperature increase. In some embodiments, the sheath can be made of a urethane polycarbonate, or another form of urethane, or another plastic or non-plastic material that provides similar properties (such as a similar modulus of elasticity, modulus of rigidity (shear modulus), and/or bulk modulus). In such embodiments, during the insertion of the sheath into a patient, the sheath can absorb heat from the body of a patient or from other heat sources, and in response, reduce its rigidity. Such reduced rigidity can increase comfort to the patient, and/or reduce the likelihood of injury or tissue damage to the patient during the insertion and use of the sheath. In some embodiments, the sheath body 40 can be made of a material capable of withstanding the relative high pressures (e.g., 300 psi) and flow rates (e.g., 130 ml/min.) associated with power injection.

Examples of bio-compatible materials that can be used for the sheath body 40, and that can include one or more of the properties described herein, such as flexibility, power injectable, and/or increased flexibility upon exposure to heat, are manufactured by AdvanSource Biomaterials Corp. (e.g., ChronoFlex C®) and Lubrizol (e.g., Carbothane TPU®). In some cases, even when the sheath material is selected to have certain properties, such as flexibility, the sheath can still kink when bent to a certain extent, for example, about 90 degrees. The method described herein can advantageously produce sheaths having improved flexibility, memory, kink-resistance and/or resilience.

In some embodiments, a sheath can be formed by extruding a selected material, for example, a polycarbonate-urethane copolymer as described herein, to form a medical article or tube and then annealing the extruded tube. Some polymers can be formed to include a mixture of crystalline regions and amorphous regions. Annealing can generally increase the crystallinity of a material and can involve heating the material to a temperature below its melting point, maintaining that temperature for a time period, and then cooling the material. The heat can provide energy to break existing bonds in the material so that atoms in the material can diffuse, redistribute, and form new bonds to create a more crystalline or organized structure. In some embodiments, an extruded tube can be annealed by heating the tube to a temperature of about 248° F. and maintaining the temperature for about one hour. Other durations and temperatures below the selected material's melting point are also possible.

Annealing can be used to change a material's structural or mechanical properties, such as strength and hardness. Annealing typically results in a more rigid material due to the increased crystallinity. However, when a polycarbonate-urethane copolymer extruded tube as described herein was annealed under certain conditions, the tube was found to have improved kink-resistance. For example, a tube extruded and annealed according to embodiments of the present disclosure was able to bend up to about 120 degrees before kinking. The process described herein can therefore be used to increase the flexibility of the tube. Alternatively or additionally, the process may provide the tube with greater kink or crease-resistance properties.

In one embodiment, a method of using a medical article having a flexible shaft made of annealed urethane polycarbonate includes inserting the shaft into a vessel over a guidewire, withdrawing the guidewire, and bending the shaft to lie substantially parallel to the skin, and retaining the shaft in the bent position without kinking the shaft. In such an embodiment, once the shaft is placed into a vessel, the shaft may be bent to lie across the skin so that it can be secured to the skin (e.g. with tape or another securement device) during use without kinking.

The extruded tube can be cut into desired lengths before or after annealing. The annealing process may alter the tube dimensions to some extent, for example, the tube may shrink slightly. Therefore, in some embodiments, if the extruded tube is cut before annealing, possible changes in dimension due to subsequent annealing are taken into account when cutting the tube. Additionally or alternatively, the tube can be rough cut before annealing and then trimmed to its desired length (e.g., 80 mm) afterward.

Methods for forming a more flexible or more kink-resistant tube as described herein can be used to form tubes for numerous applications. For example, the method can be used to form a sheath for a vascular access device as described herein. For this and other similar applications, the method can include additional steps to shape the tube for use. For example, the method can include flaring an end of the tube. This end is configured to be outside of the patient in use. The flare can then be over-molded onto a hub that will be part of the access device. The method can also or alternatively include forming an end of the tube into a tip. This end is configured to be inserted into the patient in use.

Figure 4:
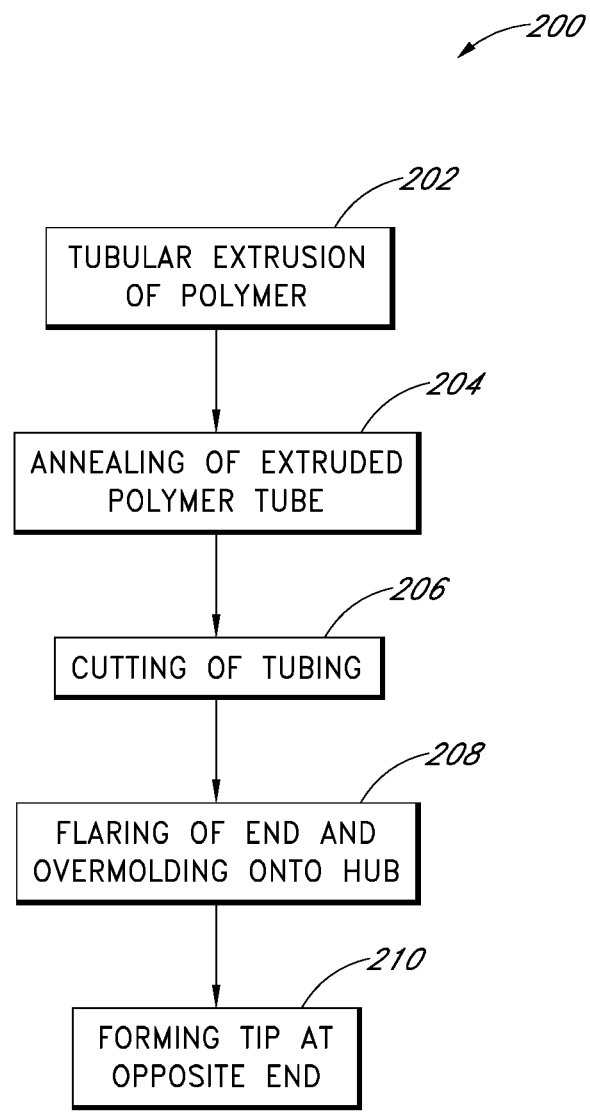
FIG. 4 shows a flow chart of an example method for forming a vascular sheath.

FIG. 4 illustrates an example method 200 of forming a flexible medical article as described herein. The method 200 includes forming a section of material out of a selected polymer. The section can be made by an extrusion process as illustrated in operation block 202. In alternative embodiments, the flexible material article can be made by injection molding, compression molding, or similar techniques. In some embodiments, a method for forming the flexible medical article includes extruding a polymer, for example, a polycarbonate-urethane copolymer or another form of urethane, to form a tubular shaft with at least one lumen. In another embodiment, the flexible medical article can be made without a lumen.

With reference to FIG. 4, in a tubular extrusion process 202, raw polymeric material can be melt processed into a barrel of an extruder. In some embodiments, the polymeric material can be made a polycarbonate-urethane copolymer or another form of urethane. It should be appreciated that one or more polymers or a composite polymer can be used in conjunction with formation method 200. Melt processing can occur by taking raw material in the form of nurdles or small beads and gravity feeding them from a top mounted hopper into the barrel of the extruder. Once inside the barrel, the material can come in contact with a rotating screw, forcing the polymeric material forward into the barrel. Heaters in the barrel and/or the pressure and friction within the barrel can heat the polymeric material to a desired melt temperature. At the front of the barrel, the melted material can leave the screw and enter into a die used to form the tubular cross-section. A hollow cross-section for the tubular member can be extruded by placing one or more pins inside of the die to produce a desired number of lumens. The size and shape of the lumens can be adjusted by size and shape of the pins as well as by adding positive pressure to the individual pins.

With continued reference to FIG. 4, once the polymer tube has been formed, the method can include heat treating the tube by annealing, as illustrated in operation block 204, to improve the kink or crease-resistance properties of the tube. Annealing can involve heating the material to a temperature below its melting point, maintaining that temperature for a time period, and then cooling the material. In some embodiments, an extruded tube can be annealed by heating the tube to a temperature of about 248° F. and maintaining the temperature for about one hour. Other durations and temperatures below the selected material's melting point are also possible. In one embodiment a tube extruded and annealed according to embodiments of the present disclosure can bend up to about 120 degrees without kinking. In another embodiment, a tube extruded and annealed according to the embodiments of the present disclosure can withstand pressures up to 300 psi and flow rates of up to 130 ml/min. In some embodiments, the polymer has increased flexibility (i.e., reduced rigidity) upon exposure to heat.

With further reference to FIG. 4, in some embodiments, the method can include sizing the tubing as illustrated in operation block 206. Sizing of the tubing can be done by cutting, machining, abrasive processing (e.g., grinding or etching), or the like. In one embodiment, following sizing of the tubing, the tubing can be further processed (e.g., be polished or sanded) to remove any sharp edges or burrs. The sizing of the tubing can be performed either before or after the annealing step illustrated in operation block 206. As described above, the annealing process may alter the dimensions of the tube (e.g., shrinkage). Thus, if the tubing is sized prior to annealing, the dimensional changes due to annealing can be taken into account when sizing the tubing. Additionally or alternatively, the tube can be rough cut to an approximate size before annealing and then trimmed to its desired length (e.g., 80 mm) after annealing.

With continued reference to FIG. 4, in some embodiments, the method 200 can also include flaring an end of the tube as illustrated in operation block 208. The flared end can then be over-molded onto a hub that will be part of the access device. Additionally or alternatively, the method 200 can include forming an end of the tube into a tip (e.g., the opposite end of the flared end of the tube) as illustrated in operation block 210. This end is configured to be inserted into the patient in use.

As used herein, the terms "tube," "tubular," and the like are meant to be broad enough to refer to structures having at least one lumen, including structures that have (i) one or more lumens (e.g., multiple lumens); (ii) one or more lumens offset from a central longitudinal axis of the structure; (iii) a single lumen structure having a generally uniform wall thickness; and (iv) a single lumen that is coaxial with a central longitudinal of the structure. Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding whether these features, elements and/or states are included or are to be performed in any particular embodiment.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above.

What is claimed is:

1. A medical article having a flexible, tubular member with at least one lumen, the tubular member being formed by a process comprising:
forming a tubular member of a medical article by extruding a polycarbonate urethane copolymer;
annealing the extruded tubular member to increase flexibility of the tubular member; and
coupling a hub to a first end of the annealed tubular member.

2. The medical article of claim 1, wherein annealing comprises annealing the tubular member at about 120° C. for about one hour.

3. The medical article of claim 1, wherein the tubular member is annealed sufficiently so as to be capable of bending up to about 120° without kinking.

4. The medical article of claim 1, wherein the polycarbonate urethane copolymer is capable of withstanding pressures up to 300 psi.

5. The medical article of claim 1, wherein the polycarbonate urethane copolymer is capable of withstanding flow rates of up to 130 ml/min.

6. The medical article of claim 1, wherein the polycarbonate urethane copolymer has increased flexibility upon exposure to a temperature of 37° C.

7. The medical article of claim 1 further comprising a dilator having a dilator shaft extending from a dilator hub, and wherein the tubular member is coaxially disposed on the dilator shaft with the hub juxtaposed the dilator hub.

8. The medical article of claim 7 further comprising:
a needle having a needle shaft and a needle hub; and
a guidewire,
wherein the dilator shaft is coaxially disposed on the needle shaft with the needle hub and dilator hub juxtaposed and the guidewire is at least partially disposed in the needle.

9. The medical article of claim 8 further comprising a track along which the needle hub travels, the track being attached to the dilator hub.

10. The medical article of claim 7, wherein the dilator shaft and dilator hub are sized to allow a needle shaft, a guidewire, or both to extend through the dilator shaft and dilator hub.

11. The medical article of claim 1, wherein the process further comprises cutting the tubular member after annealing.

12. The medical article of claim 1, wherein the process further comprises flaring the first end of the tubular member.

13. The medical article of claim 1, wherein the process further comprises over-molding the hub onto the first end of the tubular member.

14. The medical article of claim 1, wherein the process further comprises forming a second end of the tubular member into a tip.

15. The medical article of claim 1, wherein the process further comprises a step of cutting the extruded tubular member into a desired length after the step of forming the tubular member by extruding the polycarbonate urethane copolymer.

16. The medical article of claim 15, wherein the process further comprises a step of forming a second end of the tubular member into a tip after the step of annealing the extruded tubular member.

17. The medical article of claim 16, wherein annealing comprises annealing the tubular member at about 120° C. for about one hour.

18. The medical article of claim 16, wherein the process further comprises flaring the first end of the tubular member to be coupled to the hub and over-molding the hub onto the flared end.

19. The medical article of claim 16, wherein the polycarbonate urethane copolymer is selected to have the property of reduced rigidity when exposed to a temperature of 37° C.

20. The medical article of claim 15, wherein the process further comprises annealing the tubular member at about 120° C. for about one hour.

21. The medical article of claim 15, wherein the process further comprises flaring the first end of the tubular member to be coupled to the hub and over-molding the hub onto the flared end.

22. The medical article of claim 15, wherein the polycarbonate urethane copolymer is selected to have the property of reduced rigidity when exposed to a temperature of 37° C.

23. A method of using a medical article having a flexible tubular member being formed by a process comprising forming a tubular member by extruding a polycarbonate urethane copolymer and annealing the extruded tubular member to increase flexibility of the tubular member, the method of using comprising:
- inserting at least a portion of the tubular member into a vessel of a patient over a guidewire;
- withdrawing the guidewire from the vessel of the patient;
- bending the tubular member to lie substantially parallel to a skin of the patient; and
- retaining the tubular member in the bent position without kinking the tubular member.

* * * * *